July 4, 1972 L. LENS Plant Pat. 3,227
ROSE PLANT
Filed Oct. 8, 1970
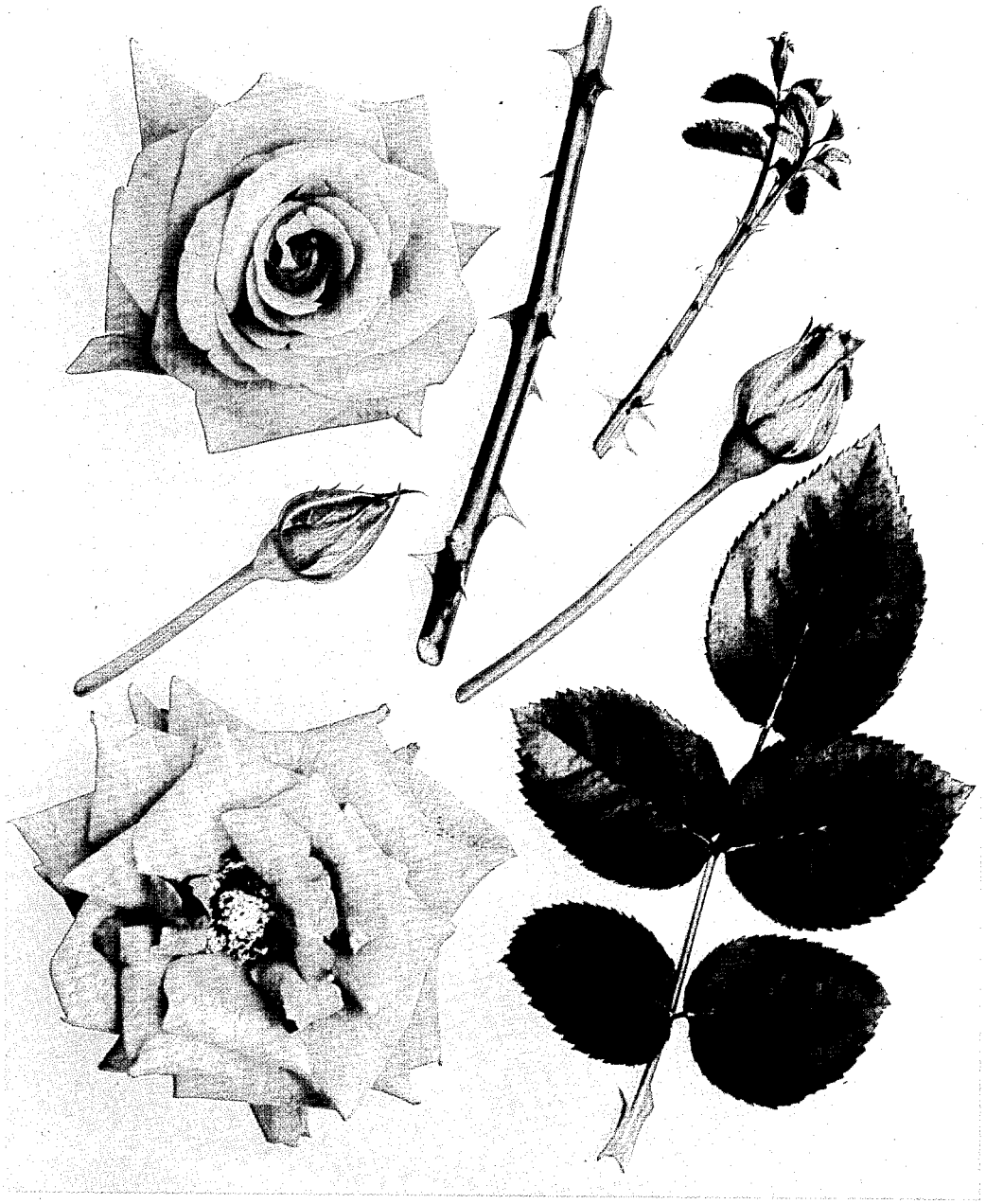
Inventor.
Louis Lens
By: Robb & Robb
Attorneys

United States Patent Office

Plant Pat. 3,227
Patented July 4, 1972

3,227
ROSE PLANT

Louis Lens, O. L. Vrouwe Wavre, Belgium, assignor to Jackson & Perkins Company, Medford, Oreg.

Filed Oct. 8, 1970, Ser. No. 79,366
Int. Cl. A01h 5/00
U.S. Cl. Plt.—20 1 Claim

The present invention relates to a new and distinct variety of rose plant of the hybrid tea class, which was originated by me as a self-pollinated seedling of the rose variety originally known in Europe as "Coloranja," but commercially known in the United States as "Mustang" (U.S. Plant Pat. No. 2,657).

The primary objective of this breeding was to produce a new and improved rose variety of the hybrid tea class which bears large, evenly colored flowers of good opening form and of a nearly orange general color tonality. This objective was fully achieved, along with other desirable features, as evidenced by the following unique combination of characteristics which are outstanding in the new variety and which distinguish it from its parent "Mustang," as well as from all other rose varieties of which I am aware:

(1) A moderately vigorous bush habit;
(2) Leathery, non-glossy, attractive foliage;
(3) Large flowers of a form similar to that of its parent "Mustang";
(4) An exceptionally clear, uniform and pure Vermilion flower color which lightens slightly to Dutch Vermilion as the flowers mature; and
(5) An excellent flower petal substance which produces a long-lasting effect both on the plant and as cut flowers, with the outer petals being of good quality and requiring no "cleaning" when used as cut flowers.

Asexual reproduction of my new variety by budding, as performed by me in Belgium and also on my behalf at Wasco, Calif., U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character. Due to unavoidable inherent photographic deviations, the red flower colors appear in the drawing as somewhat more greyed and less orange than described in the following description which is more accurate. The blossom colors are well illustrated in the drawings of Plant Patent No. 1,760, for the variety, Torch Song.

The following is a detailed description of my new rose variety, with color terminology in accordance with Wilson's Horticultural Colour Chart, except where general color terms of ordinary dictionary significance are obvious:

Parentage Seedling.
*Seed parent.*—"Mustang."
*Pollen parent.*—"Mustang."
Classification:
*Botanical.*—*Rosa hybrid.*
*Commercial.*—Hybrid tea.
Propagation: Holds its distinguishing characteristics through succeeding propagations by budding.

*Flower*

(Observations made from specimens grown in a greenhouse during the afternoon about mid-September at Irvine, Calif., U.S.A.)

Blooming habit: Recurrent—continuous.
Bud:
*Size.*—Medium; from 1 inch to 1¼ inches.
*Form.*—Ovoid.
*Color.*—When sepals first divide—Cardinal Red, Plate 822—when half-blown—inside of petals—Uniform Vermilion, Plate 18 on most of petal, with small area of Citron Green, Plate 763/3 at base of petal—reverse of petals—Geranium Lake, Plate 20/1.
*Sepals.*—Normally appendaged; smooth edge. Color—inside—Scheele's Green, Plate 860, with white tomentum, outside—Scheele's Green, Plate 860/2.
*Receptacle.*—Color—Scheele's Green, Plate 860/2. Shape—funnel. Size—small. Surface—smooth.
*Peduncle.* — Length — long. Surface — smooth. Strength—stiff; heavy. Color—Scheele's Green, Plate 860/2.
*Opening.*—Petals roll back slowly; tips slightly curled; retains high center until fully open.
Bloom:
*Size.*—Large; from 4 inches to 4½ inches.
*Borne.*—Singly.
*Stems.*—Medium length.
*Form (when first open).*—High-centered.
*Petalage.*—Number of petals under normal conditions—from 35 to 40.
*Color.*—Exceptionally uniform on all areas of each petal; all petals from outermost to center are the same color. Center of flower—upper side of petals—Dutch Vermilion, Plate 717/1. Reverse side of petals—Geranium Lake, Plate 20/1. Base of petals—small areas of Citron Green, Plate 763/3. General tonality from a distance—Vermilion, Plate 18. Discoloration—general tonality at end of first day—Dutch Vermilion, Plate 717/1. Third day—Dutch Vermilion, Plate 717/1.
*Fragrance.*—None.
Petals:
*Texture.*—Thick.
*Appearance.*—Inside—satiny. Reverse—satiny.
*Shape.*—Round.
*Form.*—Tips slightly recurved.
*Arrangement.*—Imbricated.
*Petaloids in center.*—Few; large.
*Persistence.*—Drop off cleanly.
*Lasting quality.*—On the plant—long. As cut flower—long.

*Reproductive organs*

Anthers: Large; regularly arranged around styles. Color—Yellow edges, with center Geranium Lake, Plate 20/2.
Filaments (threads): Medium length. Color—Reddish brown.
Pollen: Color—Lemon yellow.
Styles: Loosely separated; of uneven length.
Stigmas: Color—Yellow.
Ovaries: All enclosed in calyx.
Fruit: None observed.

*Plant*

Form: Bush.
Growth: Medium upright.
Foliage: Compound of 5 leaflets on normal mid-stem leaves.
*Size.*—Large.
*Quantity.*—Normal.
*Color.*—New foliage—darker than Purple Madder, Plate 1028. Old foliage—slightly deeper than Spinach Green, Plate 0960.

*Leaflets.*—Shape—oval. Texture—upper side—leathery; under side—smooth. Ribs and veins—ordinary. Edge—serrated. Serration—single; small. Petiole—Color—Green; Under side—Prickly.

*Stipules.*—Short; many small glands.

*Disease resistance.*—Resistent to mildew, as determined by comparison with other rose varieties grown under the same normal conditions at Irvine, California, U.S.A.

Wood:

*New wood.*—Color—slightly deeper than Scheele's Green, Plate 860. Bark—smooth.

*Old wood.*—Color—same as new wood. Bark—smooth.

Thorns:

*Thorns.*—Quantity—on main stalks from base—ordinary; on laterals from stalk—ordinary. Form—Broad base; long; hooked downward. Color (when young)—Green. Position—Irregular.

*Prickles.*—Quantity—on main stalks—few; on laterals—few. Color—Green.

*Short needles.*—Quantity—on main stalks—none; on laterals—none.

I claim:

1. A new and distinct variety of rose plant of the hybrid tea class, substantially as herein shown and described, characterized particularly as to novelty by the unique combination of a moderately vigorous bush habit, leathery, non-glossy, attractive foliage, large flowers of a form similar to that of its parent "Mustang" (U.S. Plant Patent No. 2,657), an exceptionally clear, uniform and pure Vermilion flower color which lightens slightly to Dutch Vermilion as the flowers mature, and an excellent flower petal substance which produces a long-lasting effect both on the plant and as cut flowers, with the outer petals being of good quality and requiring no "cleaning" when used as cut flowers.

No references cited.

ROBERT BAGWILL, Primary Examiner